(12) United States Patent
Liang

(10) Patent No.: US 9,277,863 B2
(45) Date of Patent: Mar. 8, 2016

(54) METHODS AND SYSTEMS FOR AUTOMATED MEASUREMENT OF THE EYES AND DELIVERING OF SUNGLASSES AND EYEGLASSES

(71) Applicant: PERFECT VISION TECHNOLOGY, Ltd., Tsuen Wan, N.T. (HK)

(72) Inventor: Junzhong Liang, Fremont, CA (US)

(73) Assignee: Perfect Vision Technology (HK) Ltd., Tsuen Wan, N.T. (HK)

( * ) Notice: Subject to any disclaimer, the term of this patent is extended or adjusted under 35 U.S.C. 154(b) by 432 days.

(21) Appl. No.: 13/687,309

(22) Filed: Nov. 28, 2012

(65) Prior Publication Data

US 2013/0100410 A1    Apr. 25, 2013

Related U.S. Application Data

(63) Continuation-in-part of application No. 13/116,262, filed on May 26, 2011, now Pat. No. 8,419,185, which is a continuation of application No. PCT/US2009/066148, filed on Nov. 30, 2009.

(60) Provisional application No. 61/200,494, filed on Dec. 1, 2008, provisional application No. 61/208,045, filed on Feb. 20, 2009.

(51) Int. Cl.
| | | |
|---|---|---|
| *A61B 3/10* | (2006.01) | |
| *A61B 3/18* | (2006.01) | |
| *A61B 3/00* | (2006.01) | |
| *G02C 7/02* | (2006.01) | |

(52) U.S. Cl.
CPC ............... *A61B 3/18* (2013.01); *A61B 3/0025* (2013.01); *G02C 7/02* (2013.01); *G02C 2202/22* (2013.01)

(58) Field of Classification Search
CPC ........ A61B 3/103; A61B 3/1015; A61B 3/14; A61B 3/12; A61B 3/032; A61B 3/024; A61B 3/04; G02C 13/003
USPC .......... 351/205–206, 223, 227–230, 233, 239, 351/246
See application file for complete search history.

(56) References Cited

U.S. PATENT DOCUMENTS

| | | | |
|---|---|---|---|
| 2,021,812 A | | 11/1935 | Scott |
| 3,431,688 A | | 3/1969 | Rudd et al. |
| 5,434,707 A | * | 7/1995 | Dalzell et al. ............ 359/485.04 |
| 5,652,638 A | | 7/1997 | Roffman et al. |

(Continued)

FOREIGN PATENT DOCUMENTS

| | | |
|---|---|---|
| CN | 2031935 | 2/1989 |
| CN | 1781443 A | 6/2006 |

(Continued)

OTHER PUBLICATIONS

International Search Report and Written Opinion dated Jun. 25, 2010 for PCT Application No. PCT/US2009/066148.

(Continued)

*Primary Examiner* — James Greece
(74) *Attorney, Agent, or Firm* — The Mueller Law Office, P.C.

(57) ABSTRACT

The present invention provides methods, devices, and systems for automated measured correction of the eyes and provision of sunglasses and eyeglasses for individuals, including individuals with a visual acuity of 20/20 or better.

37 Claims, 10 Drawing Sheets

(56) References Cited

U.S. PATENT DOCUMENTS

| | | |
|---|---|---|
| 5,777,719 A | 7/1998 | Williams et al. |
| 6,142,625 A | 11/2000 | Sawano et al. |
| 8,214,265 B2 | 7/2012 | Peters |
| 8,219,466 B2 | 7/2012 | Gui et al. |
| 8,229,806 B1 | 7/2012 | Chapman et al. |
| 8,235,247 B2 | 8/2012 | Alvarez |
| 8,276,735 B2 | 10/2012 | Georgens |
| 2004/0054358 A1 | 3/2004 | Cox et al. |
| 2004/0263786 A1 | 12/2004 | Williams et al. |
| 2005/0200809 A1 | 9/2005 | Dreher et al. |
| 2006/0023163 A1* | 2/2006 | Foster .......................... 351/246 |
| 2006/0203198 A1 | 9/2006 | Liang |
| 2006/0235369 A1 | 10/2006 | Macrae et al. |
| 2006/0279699 A1 | 12/2006 | Liang |
| 2007/0159593 A1 | 7/2007 | Hibino et al. |
| 2008/0018855 A1 | 1/2008 | Larichev et al. |
| 2008/0126809 A1 | 5/2008 | Rothschild |
| 2008/0143960 A1* | 6/2008 | MacRae ........................ 351/230 |
| 2008/0143963 A1 | 6/2008 | Lindacher |
| 2009/0128901 A1 | 5/2009 | Tilleman et al. |
| 2009/0244480 A1 | 10/2009 | De Gaudemaris et al. |
| 2009/0323020 A1 | 12/2009 | Zhao et al. |
| 2010/0074477 A1 | 3/2010 | Fujii et al. |
| 2010/0283963 A1 | 11/2010 | Giraudet et al. |
| 2011/0228225 A1 | 9/2011 | Liang |
| 2012/0253837 A1 | 10/2012 | Cashman et al. |
| 2012/0271412 A1 | 10/2012 | Feingold et al. |

FOREIGN PATENT DOCUMENTS

| | | |
|---|---|---|
| GB | 1463107 A | 2/1977 |
| JP | 554131950 | 10/1979 |
| JP | S601604 A | 1/1985 |
| JP | H03229212 | 10/1991 |
| JP | H05332720 A | 12/1993 |
| JP | H06034920 | 2/1994 |
| JP | H0915541 A | 1/1997 |
| JP | H10175149 A | 6/1998 |
| JP | 11056779 A | 3/1999 |
| JP | H11267100 A | 10/1999 |
| JP | H11295668 | 10/1999 |
| JP | 2002156611 | 5/2002 |
| JP | 2003140094 | 5/2003 |
| JP | 2006178245 A | 7/2006 |
| JP | 2006517135 A | 7/2006 |
| JP | 2007240553 A | 9/2007 |
| JP | 2009521726 A | 6/2009 |
| WO | 2005040896 A1 | 5/2005 |
| WO | 2007075975 A2 | 7/2007 |
| WO | 2008049503 A2 | 5/2008 |
| WO | 2009123700 A | 10/2009 |
| WO | 2010065475 A | 6/2010 |
| WO | 2012054651 A | 4/2012 |

OTHER PUBLICATIONS

Notice of Allowance dated Feb. 22, 2013 for U.S. Appl. No. 13/116,262.
Office Action dated Sep. 19, 2013 for U.S. Appl. No. 13/682,527.
Extended European Search report dated May 13, 2014 for EP Aplication No. 09830937.0.
International Search Report and Written Opinion dated Apr. 9, 2014 for PCT Patent Application No. PCT/US2013/071763.
Notice of Allowance dated May 12, 2014 for U.S. Appl. No. 13/682,527.
Office action dated May 13, 2014 for Japanese Application No. 2011-538720.
Pretrial ReExamination Report dated Nov. 28, 2014 for Japanese Patent Application No. 2011-538720.
International Search Report and Written Opinion dated Nov. 28, 2013 for PCT Application No. PCT/IB2013/001051.
Japanese Office Action dated Oct. 29, 2013 for JP Application No. 2011-538720.
Office Action dated Nov. 10, 2015 for Japanese patent application No. 2011-538720.
Office Action dated Sep. 30, 2015 for U.S Appl. No. 14/465,755.

* cited by examiner

Misaligned   Eye aligned   Phoroptor
             to the        aligned to
             Phoroptor     the Eye

METHODS AND SYSTEMS FOR AUTOMATED MEASUREMENT OF THE EYES AND DELIVERING OF SUNGLASSES AND EYEGLASSES

CROSS-REFERENCE TO RELATED APPLICATIONS

The present invention is a continuation-in-part of U.S. Patent Publication No. US2011/0228225 (U.S. Ser. No. 13/116,262) entitled "Methods and Devices for Refractive Correction of the Eyes" by Liang, filed May 26, 2011, which is a continuation of International PCT Application No. PCT/US09/66148, filed Nov. 30, 2009, which claims the benefit of U.S. Provisional Patent Application No. 61/200,494, filed Dec. 1, 2008 and U.S. Provisional Patent Application No. 61/208,045 filed Feb. 20, 2009, and all of which are incorporated herein by reference.

FIELD OF THE INVENTION

The invention relates generally to automated measured correction of the eyes so as to provide sunglasses and eyeglasses to improve an individual's vision, including individuals possessing a visual acuity of 20/20 or better.

BACKGROUND OF THE INVENTION

Refractive corrections for human eyes can be characterized into two general categories. The first category is the conventional method of vision correction which corrects for the eye's focus error and cylindrical error as measured using a manifest refraction. The second category is wavefront-guide vision correction which provides correction for all aberrations in an eye, including focus error, cylindrical error, spherical aberration, coma, and others, measured using an objective wavefront sensor.

The conventional method of vision correction is conceptually limited to a correction of just focus error and cylindrical error. In addition, it is also constrained by the subjective nature of how the manifest refraction determines the eye's refractive errors, particularly the eye's cylindrical error. Cylindrical error is also known as astigmatism, and it causes particular problems because it includes both a cylindrical power and a cylindrical axis.

There are at least five limiting factors associated with a manifest refraction. First, manifest refraction is limited by available lenses in a phoroptor, because a manifest refraction relies on applying corrective lenses and testing vision of the eye subjectively. Focus error is usually limited to a resolution of 0.125 Diopters (D) while the cylindrical error is limited to a resolution of 0.25 D. Second, subjective determination of cylindrical axis can be problematic because a slight variation of cylindrical axis—within only a few degrees—can cause a significant performance difference for a cylindrical correction of more than 2 D. Third, human errors by either the patient or a practitioner—such as an optometrist or optician—cannot be excluded because a manifest refraction involves the subjective responses of a patient to a plurality of refractive corrections, as well as the practitioner's analysis of those subjective responses. Fourth, a manifest refraction is fundamentally a partial empirical refractive solution, because a practitioner conducting the manifest refraction determines an end point for a refractive correction in a time-consuming process. Finally, manifest refraction can also be a time consuming process because it relies on human control of vision optimization with as many as three independent variables which include a focus error, a cylindrical power, and a cylindrical axis.

The drawbacks associated with using a manifest refraction compound with the high tolerance of current lens manufacturing techniques and lead to widespread erroneous vision correction. The inaccuracy of the conventional vision correction method using a manifest refraction leads to a situation where there may be significant differences in a refractive prescription of the same eye by different practitioners, as well as in a coarse resolution of cylindrical power—as large as 0.25 D—universally prescribed for conventional vision correction. Consequently, available ophthalmic lenses in today's ophthalmic industry are also limited to lenses in 0.25 D resolution. Correcting an eye's astigmatism using conventional vision correction is further complicated by the high tolerance in fabricating conventional spectacle lenses. Moreover, it is accepted in the industry that visual acuity of 20/20 is perfect already with no need for correction. Correction of emmetropic eyes beyond 20/20 is not practical with conventional manifest refraction because the end goal of a conventional manifest refraction is to mitigate the eye's symptoms so that the tested eye can achieve corrected acuity of 20/20 acuity with selected lenses in a phoroptor, Consequently, although many configurations and methods for vision correction are known in the art, all of them suffer from one or more disadvantages. Thus, there is a need to provide automated methods and devices to achieve practical uncompromised vision correction.

SUMMARY OF THE INVENTION

In one aspect of the invention, an automated method for determining a refractive correction of an eye is provided.

Thus, certain embodiments of the present invention provide methods for providing a pair of sunglasses to an individual, including individuals with a visual acuity of 20/20 or better, comprising the steps of: 1) providing a measuring station configured for automatic data acquisition without necessary intervention from a human other than the individual, the measuring station configured to obtain an objective measurement of wave aberration from each eye of the individual; place a plurality of lenses according to the obtained an objective measurement of wave aberrations into a correction module for the individual to see through and to read at least one acuity chart; and determine a focus power of each eye through subjective refraction, wherein the subjective refraction involves subjective responses from the individual to a plurality of focus powers; 2) generating correction data for making the pair of sunglasses; 3) transmitting data for making the pair of sunglasses via an electronic media, wherein the transmitted data contains at least the correction data for making the pair of sunglasses; 4) manufacturing lenses for the sunglasses based on the correction data; 5) fitting the lenses into frames to produce finished sunglasses; and 6) providing the finished pair of sunglasses to the individual.

In some aspects of this embodiment, the pair of sunglasses provided is an over-the-counter pair of sunglasses that does not require a prescription. In some aspects, the measuring station further is configured to accept results from the individual in reading the acuity chart through the correction module for each eye, and in some aspects the measuring station further is configured to allow the individual to manually adjust the focus power of the correction device. In some aspects, the transmitting data step for making the pair of sunglasses further includes at least one of following for reviewing and checking by a human other than the individual:

a) records for the obtained an objective measurement of wave aberration from each eye of the individual, b) results of the individual in reading the acuity chart through the correction device for a plurality of focus powers.

In some aspects of this embodiment of the invention, the measuring station further is configured to determine a measured cylindrical power and cylindrical axis from the objective measurement of wave aberration. In some aspects, the measuring station further is configured to offer to and receive from the individual a selection of sunglass frames. In some aspects, the generated correction data for lenses is modified to take into account of the shape of selected sunglass frames, and in some aspects, the measuring station further is configured to take a picture of the individual with and/or without the selected pair of sunglasses.

In some aspects of the invention, the measuring station further is configured to accept payment information from the individual, and in some aspects, the measuring station further is configured to accept delivery information from the individual.

In some aspects of the invention, the measuring station further is in communication with a lens fabricator and is configured to transfer the correction data to a lens fabricator to manufacture custom lenses, and in some aspects, the lens fabricator is automated. Further, in certain aspects, the measuring station is in communication with the automated lens fabricator and is configured to transfer the correction data and delivery information from the individual to a lens fabricator to manufacture custom lenses, and in some aspects, the measuring station further is configured to offer to and receive from the individual selected sunglass frame styles.

In some aspects of this method of the invention, the automated lens fabricator is further configured to assemble the manufactured custom lenses with the selected sunglass frames, and in some aspects of this embodiment, the measuring station further is configured to accept payment information and delivery information from the individual.

In yet other aspects, the lens fabricator is not automated. In other aspects, based on the correction data for each eye, off-the-shelf lenses are selected for the individual. In other aspects, the lenses are manufactured by molding or by machining.

In yet other aspects of this embodiment, the measuring station comprises a wavefront phoroptor for measuring refractive corrections of a focus error and a cylinder error for an eye, where the wavefront phoroptor comprises: a wavefront sensing module for providing the objective measurement of aberrations of the eye, measuring wavefront slopes across a pupil, and determining wave aberration of the eye that includes at least a cylindrical axis and a cylindrical power in a resolution finer than 0.25 D; and a phoroptor module with a plurality of spherical lenses and cylindrical lenses and an acuity chart for subjectively determining the focus error of the eye. In some aspects, the cylindrical lenses are set according to the objective measurement of aberrations from the wavefront sensing module; where the subjectively determined focus error involves subjective responses by the individual to a plurality of focus powers by the eye viewing an acuity chart, and in some aspects, the wavefront sensing module measures aberrations of the eye using a lenslet array wavefront sensor. In yet other aspects, the objective measurement further includes a focus error, a spherical aberration, a coma and other high-order aberrations, and wherein the cylinder power and the cylinder angle is determined for optimized vision from the determined wave aberration across a pupil of the eye.

Yet other embodiments of the present invention provide a measuring station configured for automatic data acquisition without necessary intervention from a human other than the individual configured to: obtain an objective measurement of wave aberration from each eye of the individual; determine a measured cylindrical power and a cylindrical axis from the objective measurement of wave aberration; place a plurality of lenses according to the determined measured cylindrical power and a cylindrical axis into a correction module for the individual to see through and read an acuity chart; determine a focus power of each eye through subjective refraction, where the subjective refraction involves subjective responses from the individual to a plurality of focus power corrections; and communicate the measured cylindrical power, cylindrical axis and focus power of each eye to a lens fabricator to manufacture custom lenses or to a repository of off-the-shelf lenses.

Aspects of this embodiment of the invention include the measuring station configured further to accept results from the individual in reading the acuity chart through the correction module and/or the measuring station further configured to allow the individual to manually adjust the focus power of the correction module. In other aspects, the measuring station further is configured to transmit data for review by a human other than the individual, wherein the transmitted data includes at least one of a) records for the obtained objective measurement of wave aberration from each eye of the individual, and b) results of the individual in reading the acuity chart through the correction device for a plurality of focus powers, and in some aspects, the measuring station further is configured to take a picture of the individual.

Other embodiments of the invention provide a system for providing a pair of sunglasses to an individual, including individuals with a visual acuity of 20/20 or better, comprising: a measuring station configured for automatic data acquisition without necessary intervention from a human other than the individual obtain an objective measurement of wave aberration from each eye of the individual and determine a measured cylindrical power and a cylindrical axis from the objective measurement of wave aberration; place a plurality of lenses according to the determined cylindrical power and cylindrical axis into a correction module for the individual to see through and read an acuity chart; and determine a focus power of each eye through subjective refraction, wherein the subjective refraction involves subjective responses from the individual from a plurality of focus powers; and a lens fabricator to manufacture custom lenses or a lens repository to provide off-the-shelf lenses according to the measured cylindrical power, cylindrical axis and focus power. In some aspects, the system further comprises a database configured to receive payment and delivery information from the individual.

Other embodiments of the invention provide a method for providing a pair of sunglasses to an individual, including individuals with a visual acuity of 20/20 or better, comprising the steps of: 1) providing a measuring station to the individual, the measuring station configured to automatically and without input from a human other than the individual: obtain an objective measurement of wave aberration from each eye of the individual; determine a measured cylindrical power and a cylindrical axis from the objective measurement of wave aberration; place a plurality of lenses according to the determined cylindrical power and a cylindrical axis from the objective measurement of wave aberration into a correction device for the individual to see through and read an acuity chart; and determine a focus power of each eye through subjective refraction, wherein the subjective refraction involves subjective responses from the individual to a plurality of refractive corrections; 2) generating correction data from which to manufacture lenses; 3) manufacturing the lenses or selecting a set of off-the-shelf lenses appropriate for the correction data; 4) fitting the lenses into frames to produce finished sunglasses; and 5) providing the finished sunglasses to the individual.

Yet other embodiments of the present invention provide a kiosk system for prescriptive sunglasses or eyeglasses, configured for automatic data acquisition without necessary intervention from a human other than the individual, comprising: a wavefront sensing module for providing objective measurement of aberrations of the eye, wherein the wavefront sensing module measures wavefront slopes across a pupil and determines wave aberration of the eye that includes at least a cylindrical axis, and a cylindrical power in a resolution finer than 0.25 D; a vision correction module for presenting a plurality of refractive corrections for the individual to see through, wherein the plurality of refractive corrections includes: a cylindrical power and a cylindrical axis according to the determined wave aberrations, and a plurality of focus power corrections that is controlled manually by the individual; an acuity chart for determining visual acuity of the eye under the plurality of focus power corrections, human-to-machine interface module to accept results from the individual in reading the acuity chart through the correction module for a plurality of focus power corrections; an exporting module for communicating data to a lens fabricator to manufacture custom lenses or to a repository of off-the-shelf lenses, wherein the communicated data includes at one of the following: the measured cylindrical power, cylindrical axis and focus power of each eye; records of the wavefront module for data review; and results of the individual in reading the acuity chart through the correction device for a plurality of focus power corrections.

In another embodiment of the invention, a method of manufacture for producing an ophthalmic lens is provided, including automated methods of manufacture. In a first step, correction data including wavefront aberration and focus power lens is transmitted by a measuring station to a lens fabricator and is received by the lens fabricator. In a second step, a semi-finished blank is selected by the lens fabricator. In a third step, the semi-finished blank is placed in a lens surfacing system in the lens fabricator. In a fourth step, the surface of the semi-finished blank is surfaced based on the correction data received from the measuring station and a set of known refractive properties of the semi-finished blank to create a fabricated lens. In a fifth step, the refractive power of the fabricated lens is measured with a lensometer to determine the refractive error between the refractive power and the correction data. In a final optional step, the surface of the fabricated lens is reworked based on the determined refractive error until a measured cylindrical power of the fabricated lens and the cylindrical power of the correction data are within a tolerance of between 0.01 D and 0.08 D.

Various objects, features, aspects and advantages of the present invention will become more apparent from the following detailed description of preferred embodiments of the invention.

DETAILED DESCRIPTION OF THE PREFERRED EMBODIMENTS

Figure 1A:
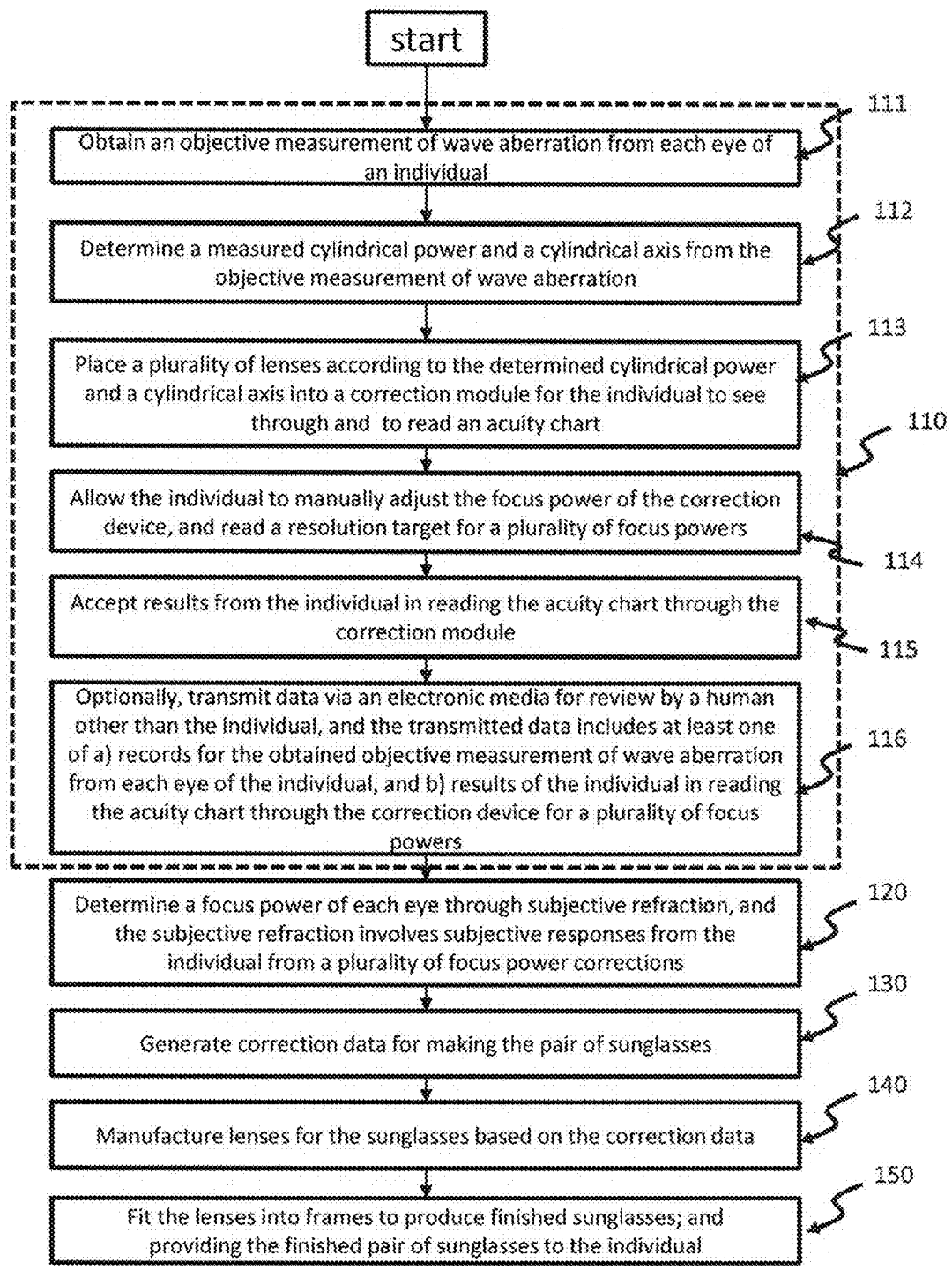
FIG. 1a shows a flow chart for a method for automated measured correction of the eye and provision of sun- or eyeglasses in accordance with one embodiment of the present invention.

Reference now will be made in detail to embodiments of the disclosed invention, one or more examples of which are illustrated in the accompanying drawings. Each example is provided by way of explanation of the present technology, not as a limitation of the present technology. In fact, it will be apparent to those skilled in the art that modifications and variations can be made in the present technology without departing from the spirit and scope thereof. For instance, features illustrated or described as part of one embodiment may be used with another embodiment to yield a still further embodiment. Thus, it is intended that the present subject matter covers such modifications and variations as come within the scope of the appended claims and their equivalents.

Automated Measurement of the Eyes

The present invention is drawn to automated methods, devices and systems to provide sunglasses and eyeglasses that allow for vision correction, even for individuals with visual acuity of 20/20 or better. The present invention particularly is revolutionary because it provides sunglasses for vision correction of emmetropic eyes, when very typically sunglasses are sold "off-the-shelf" with lenses that offer no optical correction. Though sunglasses most typically do not offer refractive correction, sunglasses are important as they offer protection from UV rays, and protection from eye discomfort due to bright light. Current sunglasses also typically offer options such as polarization for glare reduction, and various lens colors such as brown for enhanced depth perception and grey for color fidelity. The present invention is applicable for frames of any shape, and particularly applicable to sunglasses (or goggles) that have wrap shapes, as for such configuations correction of vision is important because the lens is not parallel to the cornea. Thus, in contrast to the current approach to selling sunglasses, the present invention is drawn to automated methods, devices and systems that provide sunglasses that allow for enhanced vision correction, even in individuals that have a visual acuity of 20/20 or better or in individuals who wear contact lenses for vision correction.

Emmetropia is defined as the state of vision where an object at infinity is in sharp focus with the eye lens in a neutral or relaxed state. This condition of the normal eye is achieved when the refractive power of the cornea as well as the crystalline lens and the axial length of the eye balance out, which focuses rays exactly on the retina of the eye, resulting in perfect vision. An eye in a state of emmetropia requires no correction; however, emmetropic eyes actually are not perfect. For example, FIGS. 2 and 3 demonstrate that there are optical defects for emmetropic eyes between 20/20 and 20/10. Further, sunglasses provide additional challenges for emmetropes. For example, the reduced light level due to the darkened lenses can cause problems, as can the transition from bright light to clouded or overcast conditions.

Moreover, the inventor has collected additional clinical data indicating that astigmatism (cylinder error) in eyes with an acuity of 20/10 or 20/12 can be as large as 0.60 D in some eyes as measured by a wavefront aberrometer; and that correcting an eye's astigmatism in 20/10 and 20/12 eyes showed significant medical benefits for sunglasses. It was found that both brightness and contrast improved as did depth perception. The inventor also has collected more clinical data in individuals with an acuity of 20/25, 20/20, or 20/16 showing that both focus error and cylinder error (astigmatism) are important. Astigmatism in eyes with a visual acuity of 20/25, 20/20, or 20/16 can be as large as 1.0 D in some eyes, as measured by a wavefront aberrometer; and that correcting an eye's focus error and astigmatism in eyes with a visual acuity of 20/25, 20/20, or 20/16 can improve visual acuity by 2 to 4 lines, and brightness, contrast and depth perception are improved.

FIG. 1a shows a flow chart for a method for automated measured correction of the eye and provision of sun- or eyeglasses to an individual in accordance with one embodiment of the present invention. In step 1, a measuring station or kiosk is provided. The measuring station or kiosk preferably comprises: 1) a comfortable place for the individual to sit; 2) a wavefront sensing module for providing objective measurement of aberrations of the eye; where the wavefront sensing module measures wavefront slopes across a pupil and determines wave aberration of the eye that includes at least a cylindrical axis, and a cylindrical power in a resolution finer than 0.25 D; 3) a vision correction module for presenting a plurality of refractive corrections for the individual to see through, where the plurality of refractive corrections includes a cylindrical power and a cylindrical axis according to the determined wave aberrations, and a plurality of focus powers that are controlled manually by the individual; 4) an acuity chart for determining visual acuity of the eye under the plurality of focus power corrections; 5) a human-to-machine input module for the individual to communicate with the measuring station, to accept results from the individual in reading the acuity chart through the correction module for a plurality of focus power corrections, and, optionally, to accept delivery information from the individual; 6) an exporting module for communicating data to a lens fabricator to manufacture custom lenses or to a repository of off-the-shelf lenses, where the communicated data includes at least one of the following: the measured cylindrical power, cylindrical axis and focus power of each eye; records of the wavefront module for data review; or results from the individual reading the acuity chart through the correction device for a plurality of focus power corrections; 7) optionally, an image module for taking a picture of the individual with and/or without the selected sunglass frames; and 8) optionally, an electronic payment module for accepting payment information from the individual.

The measuring station 110 is configured to: 1) automatically acquire data without intervention from a human other than the individual, by obtaining an objective measurement of wave aberration from each eye of the individual 111; 2) determine a measured cylindrical power and a cylindrical axis from the objective measurement of wave aberration 112; 3) place a plurality of lenses according to the determined cylindrical power and a cylindrical axis into a correction module for the individual to see through and read an acuity chart 113; 4) allow the individual to manually adjust the focus power of the correction device and read a resolution target for a plurality of focus powers 114; 5) accept results from the individual in reading the acuity chart through the correction module 115; and 6) optionally, transmit data via an electronic media for review by a human other than the individual 116, where the transmitted data includes at least one of a) records for the obtained objective measurement of wave aberration from each eye of the individual, and b) results of the individual in reading the acuity chart through the correction device for a plurality of focus powers.

Additionally, the measuring station is configured to determine a focus power of each eye through subjective refraction, where the subjective refraction involves the measuring station receiving subjective responses from the individual to a plurality of focus powers 120.

The measuring station of the present invention determines focus power under a cylindrical correction according to wavefront measurements. Cylinder power and cylinder axis both have an impact on subjective focus power. The advantages of determining cylinder power and cylinder axis according to wavefront measurements include eliminating the two independent knobs typically used in the art to measure subjective refraction. This provides state-of-the-art quality of vision after correction as the eye is astigmatism-free according to objective measurement of the eye's wave aberration. Focus power must be determined subjectively because the eye can accommodate for different focuses, ensuring perfect focus power avoiding overcorrection and undercorrection.

The automated measuring station of the present invention provides many advantages described above, and provides additional advantages. Traditional refractive correction requires subjective refraction for at least three parameters: focus, cylinder power and cylinder angle, and these parameters are most often measured by a professional such as an optometrist or an optician. The measurements taken are often complicated because traditional instruments have three independent knobs for vision optimization—thus, such measurements and instrumentation cannot be automated. However, the methods and devices of the present invention can be automated because cylinder angle and cylinder axis are precisely determined objectively via a wavefront aberrometer. It is well-known that conventional auto-refractions cannot distinguish image blurs caused by focus error, cylinder error (cylinder power & cylinder axis), spherical aberration, coma and a host of other high-order aberrations in the eye. When human vision is optimized in a conventional auto-refractor for the sharpest image possible, determination of the eye's cylinder power and cylinder angle is impacted by the real-time focus error (the eye's accommodation) as well as the eye's other aberrations: spherical aberration and coma. Unlike conventional auto-refractors, a wavefront aberrometer, measures all aberrations in an eye independently through a wavefront sensor. Measurement of the eye's cylinder power and cylinder axis is thus not influenced by the eye's real-time focus error such as accommodation or by spherical aberration, coma, and many other high-order aberrations. A wavefront aberrometer provides cylinder angle and cylinder power with unprecedented precision, so that they can be used as the final cylinder power and cylinder axis without the need of subjective validation as in the conventional manifest refraction. Additionally, focus power of any eye must be subjectively determined as the eye must accommodate for different distances, refraction of the eye requires only one knob, which can be manipulated by the individual patient at the measuring station.

The wavefront sensor that is part of the measuring station of the present invention can be run automatically on command, and unlike a conventional auto-refractor, it can provide wavefront sensor images for independent review so that wavefront measurement can be validated later by an individual such as a optical professional, if desired. When an automatic measurement of eye's cylinder power and cylinder angle is used for fabricating a correction lens, it is preferred in some embodiments to have an independent validation by a human other than the tested individual. Wavefront images and their analysis provide direct evidence for another individual to determine whether the automatic measurement of the cylinder angle and the cylinder power are acceptable. Conventional autorefractors do not have the necessary information for an independent validation. Additionally, for the validation and determination of focus power of the eye, it is preferred that another individual review subjective acuity for a plurality of focus powers. Otherwise, because the eye can accommodate to different focus powers, focus power determined by the tested individual based on best visual acuity alone can lead to overcorrection leading to hyperopia of the eye. In some embodiments, the methods of the present invention further comprise allowing a human other than the tested individual to review data transmitted from the measuring station and to allow the individual to send feedback data remotely to the measuring station to correct any errors in or fine tune the automatic measurements.

The measuring station of the present invention may also provide additional functionalities. For example, the measuring station may present to the individual a selection (different styles and/or sizes and/or colors) of sun- or eyeglass frames for consideration, either physical samples or virtual samples. In addition, the measuring station may take a digital photograph of the individual so that the individuals can "virtually" try on different frame styles, sizes and colors, with the digital images provided to the individual by the measuring station. Moreover, the digital images provided may serve a purpose aside from aesthetics and fashion; for example, another advantage of taking a photograph is as glasses frames are positioned on an individual's face, the lenses will be positioned in relation to the eye—more or less uniquely depending on the individual's face and the frames selected. Taking a photograph of the individual's face in combination with information about the frame style and size selected allows software associated with the measuring station to optimize alignment of the optical center of the lens with the individual's eye's pupils. Other functionalities that may be associated with the measuring station include the measuring station accepting payment from the individual, accepting prescription for an individual (to provide vision correction in accordance with a prescription with, e.g., additional vision correction as determined by the methods of the present invention), accepting delivery (e.g., shipping) information from an individual, and accepting a focus power for near vision of an individual with presbyopia so that the sunglasses can be made as bi-focal, tri-focal, and progressive lenses.

In another step of FIG. 1a, correction data based on the measured wave aberrations and focus power (correction data) is generated by the measurement station 110, or by a computer in communication with the measurement station. In another step, the correction data 130 (along with other data such as digital image, prescription, payment, delivery and/or any other pertinent data) is then transmitted from the measurement station (or computer in communication with the measurement station) via electronic media to a lens fabricator.

The lens fabricator may be a manual lens fabricator or may be an automated lens fabricator. Descriptions of lens fabrication are provided herein in the section entitled "High-precision toric lenses for refractive corrections" and in conjunction with the description of FIG. 5. Essentially, lenses are manufactured by molding or machining or a combination of the two 140. For example, semi-finished lens blanks are "generic" lenses that provide a certain range of correction, and then are typically custom finished to precise specifications based on the correction data (or prescription) for the individual. The present invention contemplates transmitting data to an automated, a semi-automated or a manual lens fabricator, where lenses are manufactured based at least on the correction data transmitted by the measurement station to the lens fabricator. In addition to fabricating the lenses, the lens fabricator may also fit the lenses into the frames of the sun- or eyeglasses 150. Finally, the finished sun- or eyeglasses are provided to the individual 150. As with the manufacturing step and the fitting step, providing the finished sun- or eyeglasses to the individual may be an automated process, a semi-automated process, or a manual process based on, e.g., delivery information provided by the individual, input into the measurement station or otherwise provided by the individual.

Improved Methods for Determining a Refractive Correction of an Eye

Figure 1B:
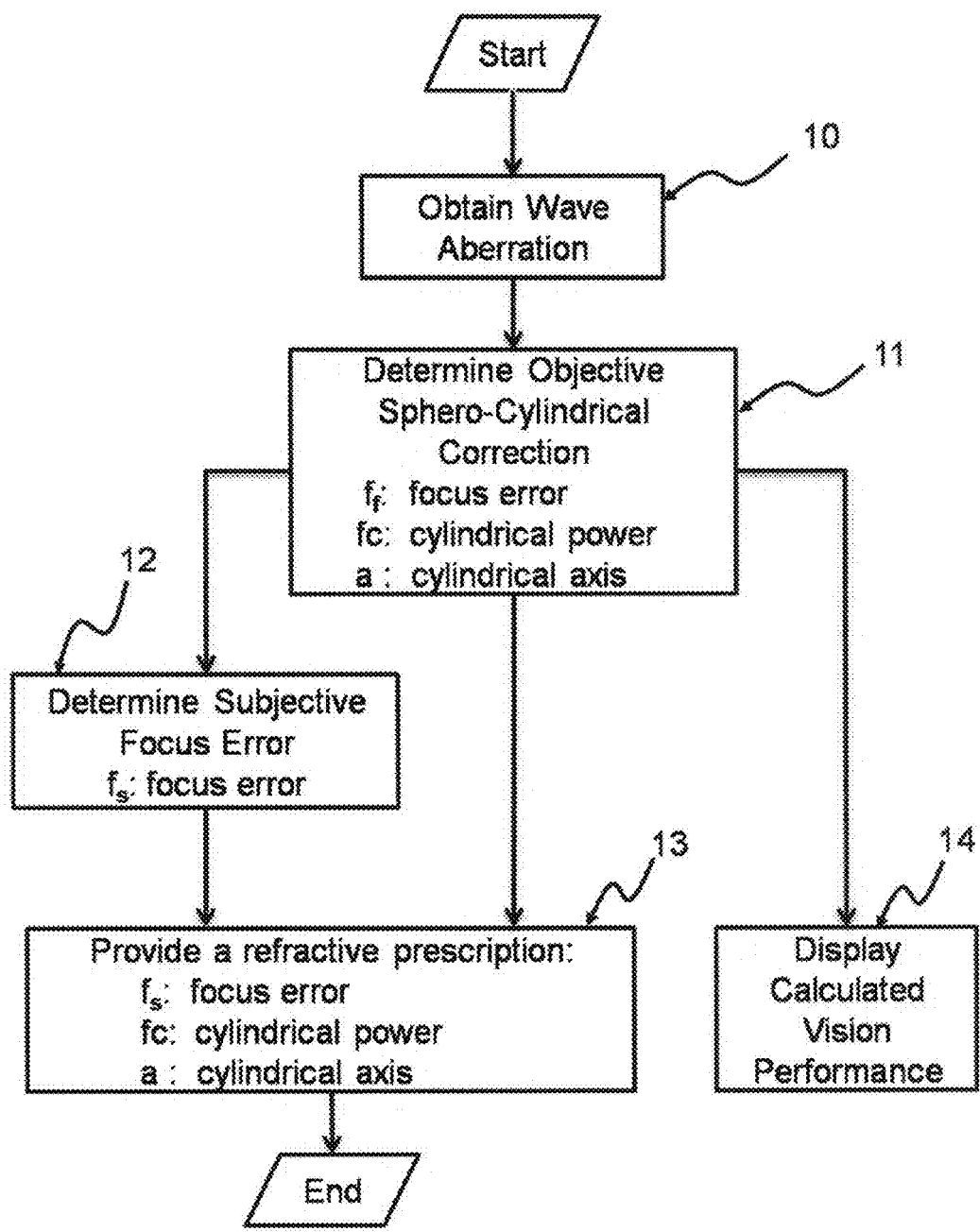
FIG. 1b shows a flow chart for a method for determining a refractive correction of an eye that is in accordance with the present invention.

FIG. 1b shows a flow chart for an improved method for determining a refractive correction of an eye based on an objective measurement of the eye's wave aberration and a subjective measurement of the eye's focus error in accordance with steps 111, 112 and 120 of FIG. 1a. This improved method enables the production of an optimized astigmatism-free refractive correction so that a majority of normal human eyes can achieve visual acuity of 20/10 instead of conventional 20/20 and provides even individuals with a visual acuity of 20/10 with corrected, enhanced vision.

First, in step 10, an objective measurement of all the aberrations in an eye is obtained, wherein all aberrations are expressed in a wave aberration $W(x,y)$. Second, in step 11, an objective sphero-cylindrical correction is determined from the obtained wave aberration by optimizing vision of the eye through removal of measured focus errors and cylindrical errors. The objective sphero-cylindrical correction comprises a focus error, a cylindrical power, and a cylindrical axis. Third, in step 12, a focus error of the eye is obtained through a subjective refraction, wherein the subjective refraction involves measuring vision performance of an eye based on subjective responses to a plurality of refractive corrections. Finally, in step 13, refractive correction data for an ophthalmic lens or refractive procedure is generated by combining the objectively determined cylindrical power, the objectively determined cylindrical axis, and the subjectively determined focus error.

The method described has many advantages in comparison to conventional vision correction. First, cylindrical error in an eye as little as 0.025 D can be precisely determined just like other high-order aberrations such as spherical aberration and coma in an eye, because the refraction process does not depend on the limited cylindrical lenses in a phoroptor, subjective feedback about the fine difference between different cylindrical corrections by the tested subjects, and subjective optimization strategies used by the practitioners. Second, the cylindrical axis can be precisely determined and a tolerance for an error in cylindrical axis can be determined from the calculated image quality of an eye. Finally, vision optimization is no longer limited to a specific situation in a manifest refraction. Instead, virtual optimization can be applied to take account of different conditions of vision at different pupil sizes through the use of vision simulation of outdoor vision, indoor vision, and night vision.

In contrast to the objective wavefront refraction using a wavefront aberrometer as described in U.S. Pat. No. 5,777,719 by Williams and Liang, the method described also addresses the issue of measuring focus error in the eye using an objective refraction. Objective wavefront sensors like a wavefront aberrometer can measure focus error accurately, but cannot guarantee that the measured focus error is the best for far vision of an eye for two reasons. First, human eyes are known to change focus power by the crystalline lens at different viewing distances, which is also called accommodation. An objective wavefront sensor can only measure the focus error of an eye at one particular accommodation state. Second, objective wavefront sensors like an objective aberrometer only measure focus error of an eye at one particular wavelength of light, which is often in the infrared spectrum to assure the patient remains comfortable during the objective refraction. Chromatic aberration for perception must be taken into account for determining the best focus for an eye for the far accommodation point. Therefore, the focus error obtained from an objective refractor could be the true focus error for the far accommodation point within +0.125 D for only about 20% of measured eyes.

About 40% of eyes will be under-corrected based on the focus error derived from an objective refractor, which will lead to a visual acuity below 20/20. At the same time, another 40% will be over-corrected based on the focus error obtained from an objective refractor, which leads to hyperopic vision after the refractive correction. The improved method for determining a refractive correction discussed here in accordance with the present invention uses a subjective approach to revise the focus error from the objective refractor, and thus takes into account both accommodation and chromatic aberration for an optimized refraction of the eye's far accommodation point.

The described improved method for determining a refractive correction can further include a preview of vision correction, as in step 14, even before an ophthalmic lens is made. Prediction of vision may include convolved retinal images of acuity charts, calculated modulation transfer functions, calculated point-spread functions, and simulation of nighttime symptoms. The calculated vision performance can be shown to a patient as well as a practitioner for accepting or selecting a specific refractive correction.

Figure 2:
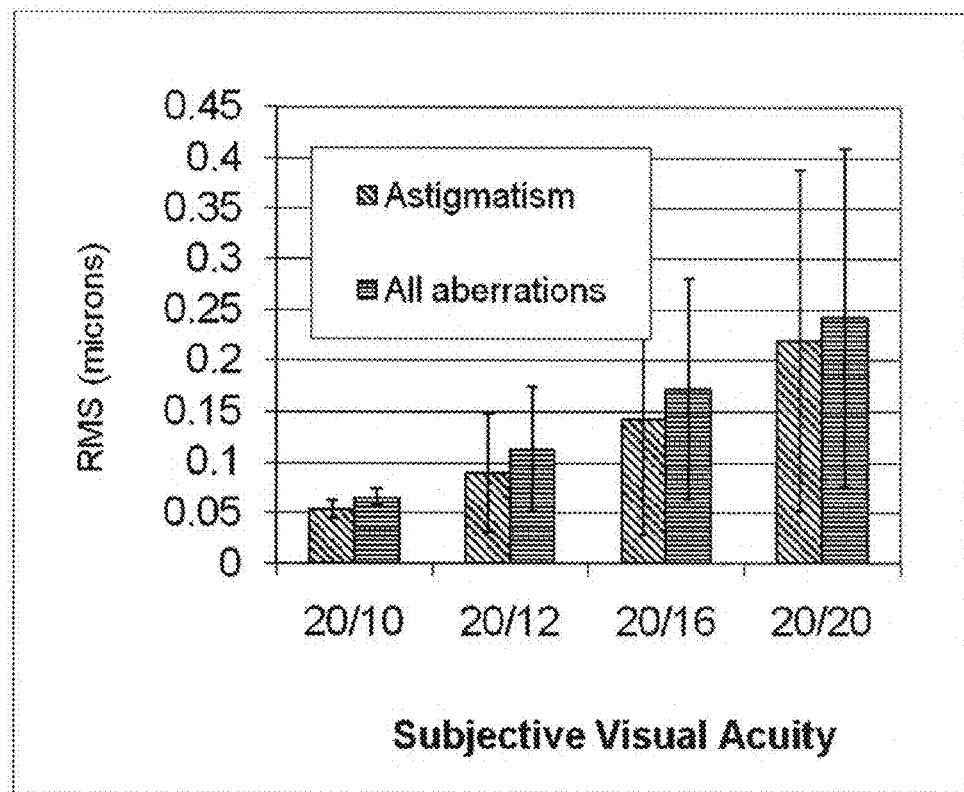
FIG. 2 shows aberrations in emmetropic eyes having subjective visual acuity better than 20/20 without any refractive correction.

The described improved method for determining a refractive correction enables an optimized astigmatism-free refraction for every eye. Perfect correction of an eye's cylindrical error can have significant impact on the visual acuity of a corrected eye. FIG. 2 shows the cylindrical error as well as the total aberration in more than 200 eyes with visual acuity better than 20/20. All the tested eyes are naturally emmetropic without any refractive correction. The cylindrical error and total aberrations in each eye are measured with an objective wavefront sensor and calculated based on the pupil size for each eye during the subjective measurement of visual acuity. The pupil size of acuity measurements ranges between 2.5 mm and 4.5 mm with an average pupil size of 3.7 mm. The error bars in FIG. 2 is one standard deviation for the measured population.

As can be seen in FIG. 2, the objectively measured cylindrical error and the subjectively measured acuity are correlated. In addition, it is clear that the cylindrical error is the dominate factor in determining subjective visual acuity.

Figure 3:
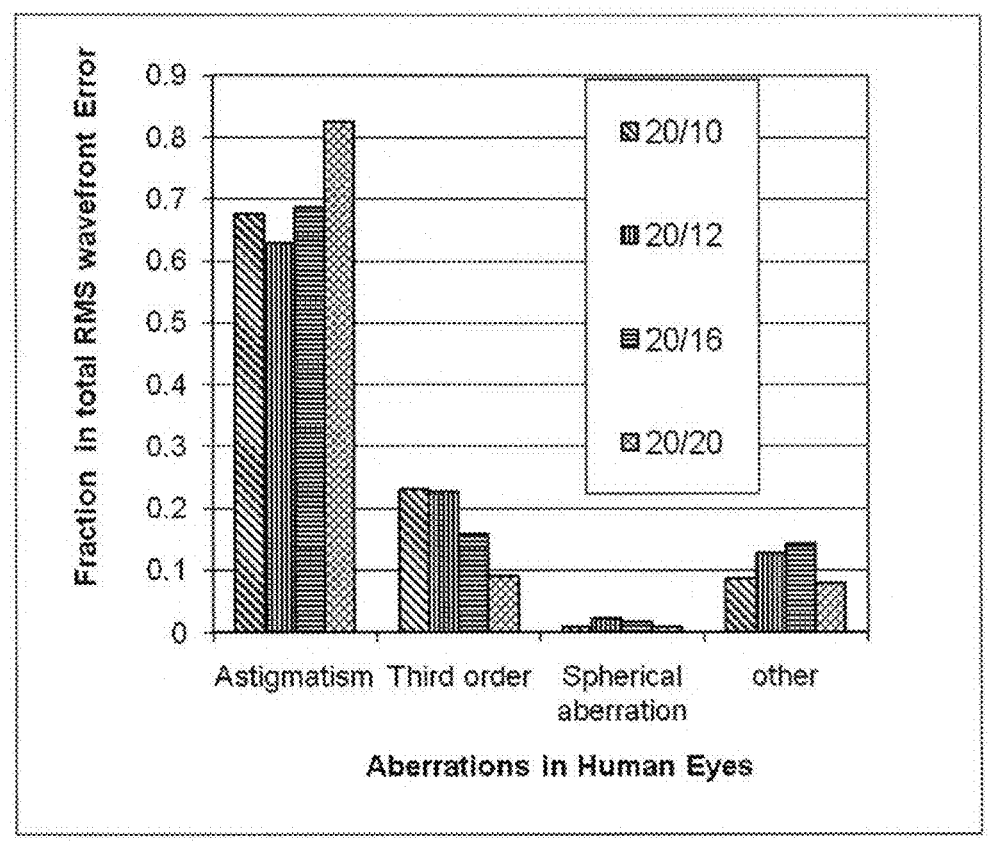
FIG. 3 shows fractions of different aberrations in the total aberration for emmetropic eyes having visual acuity better than 20/20 without any refractive correction.

FIG. 3 also highlights the importance of cylindrical error for visual acuity in naturally emmetropic eyes. FIG. 3 shows averaged fractions of different aberrations in the total aberrations for emmetropic eyes in four acuity groups in a yet to be published clinical study. It is seen that the cylindrical error accounts for 60% to 80% of all aberrations in emmetropic eyes in an acuity test. Coma has a much smaller contribution of 10% to 20%, while spherical aberration has negligible impact on visual acuity.

From the data in FIG. 2 and FIG. 3, it is not difficult to conclude that quality in correcting the cylindrical error in an eye has significant impact on subjective visual acuity. Visual acuity of 20/10 or 20/12 can usually be achieved just by a perfect correction of cylindrical error. Although important for vision at nighttime, additional correction of coma, spherical aberration, and other high-order aberrations has negligible impact on visual acuity for the majority of normal human eyes.

Perfect correction of an eye's cylindrical error requires precise measurements and specification of the cylindrical error in an eye. It is therefore necessary to specify cylindrical power much finer than the conventional resolution of 0.25 D, e.g. 0.025 D.

It is also important to record cylindrical axis in the objective measurement. One embodiment for recording the cylindrical axis is to record a digital picture of an eye while the objective measurement of cylindrical error is taken. The digital picture can later be used to assist the placement of an ophthalmic lens in an eye, or to verify proper orientation of an ophthalmic lens.

The described method for determining a refractive correction, when combined with innovations also described in the present application for advanced lens making, will enable an astigmatism free customized refractive correction that is superior in visual performance to the conventional method for vision correction based on conventional manifest refraction.

In one embodiment of the present invention, a method for obtaining an astigmatism-free customized refractive correction comprises the steps as follows. First, a wave aberration of an eye is obtaining objectively, wherein the wave aberration includes focus error, astigmatism, coma, and spherical aberration in the eye. Obtaining a wave aberration of an eye objectively can be achieved by measuring wave aberration of an eye using a device like an objective aberrometer as described in U.S. Pat. No. 5,777,719 by Williams and Liang. Second, a cylindrical power and a cylindrical axis are determined from the objectively obtained wave aberration. The resolution for the cylindrical power must be finer than 0.25 D, e.g., 0.025 D. The specification for the determined cylindrical power has a resolution between 0.01 D to 0.1 D. Cylindrical axis must also be precisely determined. Third, a focus power of the eye is determined through subjective refraction. Subjective refraction can be achieved through the use of a phoroptor presented by the measuring station or kiosk to the individual patient. Fourth, a refractive prescription for an ophthalmic lens or for a refractive procedure is generated by combining the objectively determined cylindrical power and cylindrical axis, and the subjectively determined focus power. Fifth, a pre-made lens most closely correlating to the determined cylindrical power, cylindrical axis and focus power is selected from a stock of such lenses or a customized ophthalmic lens is fabricated based on the generated high-precision refractive correction data with a high-precision cylindrical power. In preferred embodiments, the cylindrical power has a resolution finer than 0.25 D, e.g., 0.025 D, with a tolerance between 0.01 D and 0.05 D. Additionally, the refractive correction can further include a spherical aberration that is determined from the wave aberration. Reducing spherical aberration in some eyes can improve night vision, particularly for those eyes with known nighttime symptoms such as glare and halo.

Figure 4:
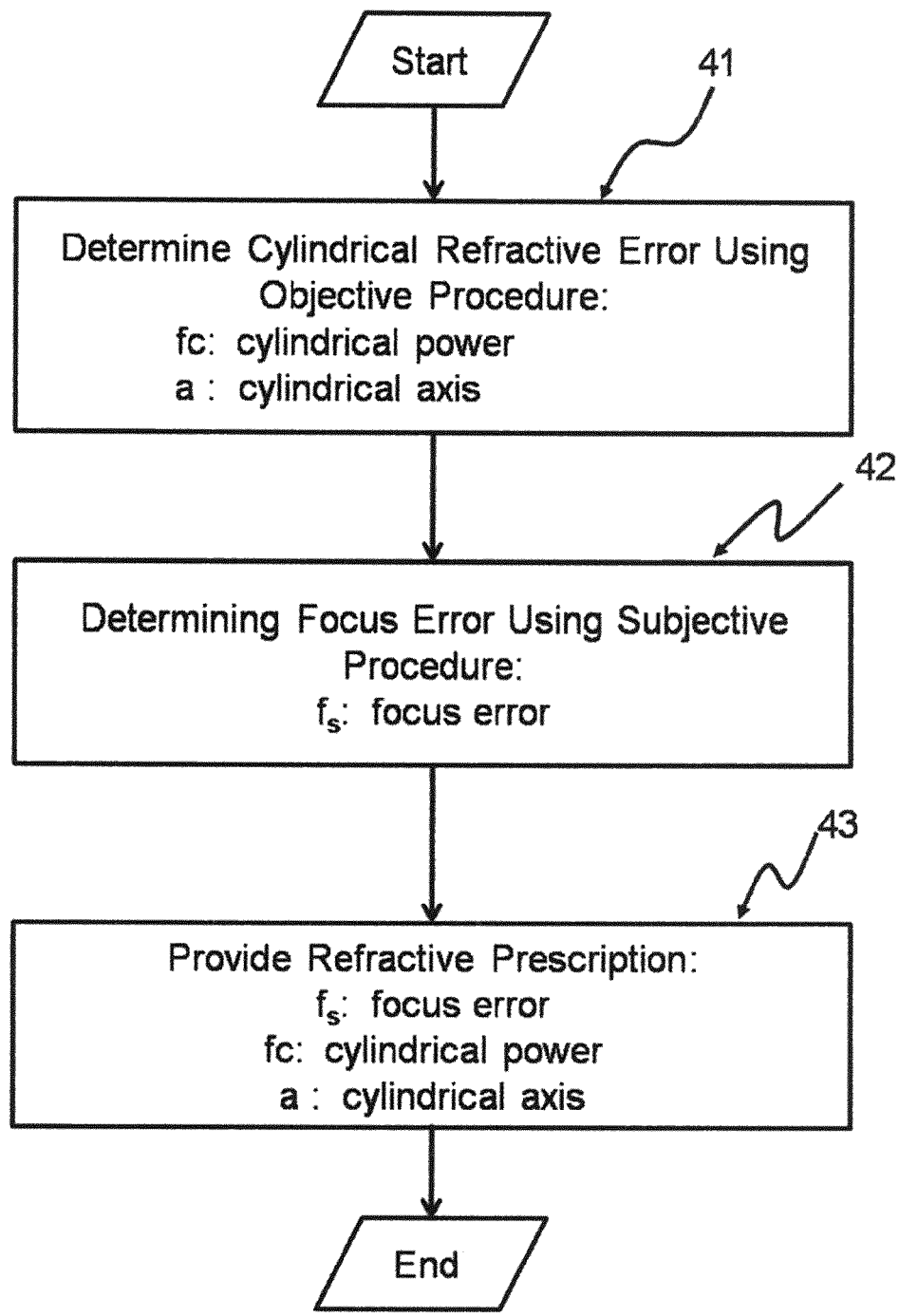
FIG. 4 shows a flow chart for a method for determining refractive correction of an eye in accordance with the present invention.

In another embodiment of FIG. 1b, a simplified method for a perfect correction of eye's cylindrical error is shown in FIG. 4. This embodiment does not involve measuring high-order aberrations such as spherical aberration and coma. First, in step 41, a cylindrical error of an eye is determined using an objective procedure without any subjective responses. For improved accuracy in determining the cylindrical error, the objective procedure in step 41 might involve measuring refractive properties of an eye in a pupil size between 2.5 mm and 4 mm pupil, and taking an average measurement for a plurality of independent objective measurements. Second, in step 42, a focus error of the eye is determined through a subjective refraction measuring vision performance of an eye based on subjective responses to a plurality of refractive corrections. Third, in step 43, correction data used to select or manufacture an ophthalmic lens is generated by combining the determined cylindrical refractive error and the determined focus error, wherein the cylindrical error has a finer resolution less than the traditional 0.25 D, e.g., 0.025 D.

High-Precision Toric Lenses for Refractive Corrections

Due to the limitations in the conventional manifest refraction, ophthalmic lenses today are made with a cylindrical power resolution of 0.25 D. Corrections of astigmatism in human eyes using real spectacle lenses is further complicated because lenses are in reality made with a relative large tolerance of between +0.09 D for low power lenses and up to +0.37 D for high power lenses. Therefore, spectacle lenses for astigmatism-free customized refractive corrections must be made using more advanced technologies.

FIG. 1a provides a step to manufacture lenses based on the correction data generated and transmitted by the measuring station. Spectacle lenses today are made using either: lens molding or lens machining using computer-controlled lathes. For the majority of spectacle lenses in a normal refraction range (spherical power between −6 D and +6 D), lenses are typically molded in batches, and stocked either in labs or in lens shops. Two lens molds are needed, and one mold has a base curve that is either spherical or aspheric in shape and the other mold has a toric shape if the spectacle lens has a cylindrical power. For lenses with a refractive power beyond the normal range, lenses are usually fabricated from semi-finished lens blanks that are molded in batches and stocked in factories. A semi-finished lens blank contains a finished base surface in a spherical or aspheric curve and a top prescription or machinable surface that will be surfaced based on the lens prescription and optical power of the base surface. If the fabricated lens has a cylindrical power, the top surface will have a toric shape.

For both molded lenses and machined lenses with a cylindrical power, the finished lenses consists of a base curve that is spherical or aspheric in shape, and a prescription or machinable curve that is toric in shape for a custom lens with a cylindrical power. The base curve is often set to one of 5 to 8 possible surface shapes, while the prescription or machinable surface must be capable of taking on the shape of one of several hundred curves in order for the combined lens to correct for different combination of spherical and cylindrical powers with the conventional resolution of 0.25 D.

For spectacle lenses with a fine cylinder resolution of 0.025 D instead of 0.25 D, manufacturers would need ten times more prescription curves if they continued to use the conventional lens shape with one toric surface. Although possible in theory, making custom lens for astigmatism-free correction using one toric surface would be prohibitively expensive because of the enormous number of molds that would be needed.

Figure 5:
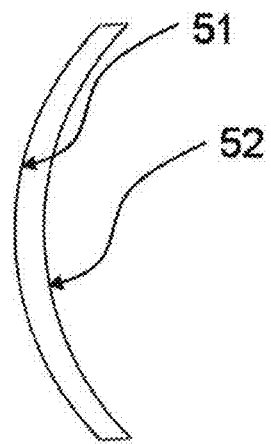
FIG. 5 shows an ophthalmic lens in accordance with the present invention.

FIG. 5 illustrates new spectacle lenses in accordance with the present invention for astigmatism-free customized refractive correction. In one embodiment of the present invention, the lens comprises a toric surface 51 that is a modified version of traditional base curves used in conventional lenses. A small amount of cylindrical power (<0.25 D) can be added to a traditional base curve for fine tuning cylindrical power at a resolution below 0.25 D. The other toric surface 52 can be the same as those used in making conventional toric lenses, which have cylindrical powers ranging from 0.00 D to 6.00 D with a resolution of 0.25 D. Both the base curve and the prescription or machinable curve can also have aspheric characteristics for reducing oblique astigmatism just like conventional toric lenses.

Two embodiments can be used for fine tuning cylindrical powers as fine as 0.025 D. One of the embodiments involves a fixed cylindrical power of 0.25 D or 0.125 D at the base curve, adjusting the angle between the two cylinder axes, and thereby achieving cylindrical power resolution as fine as 0.025 D. The other embodiment involves a plurality of cylindrical powers for each base curve (0.025 D, 0.05 D, 0.075 D, 0.10 D, 0.125 D, and 0.2 D), combining the cylindrical power from the base curve and the prescription curve, and thereby achieving fine cylindrical power as fine as 0.025 D. In the second embodiment, axes of the two toric surfaces can be made to coincide to achieve the designed cylindrical powers, or slightly different for further tuning of cylindrical powers.

For manufacturing lenses with two toric surfaces that both have cylindrical powers, it is important to control orientations of the two cylinder axes to achieve a desired cylindrical power. When a spectacle lens is molded with two toric molds, each mold can have a machine-readable mark. Two molds should be aligned on their cylinder axes before being put together to form a cavity for molding a lens. When a lens is machined for two toric surfaces, the semi-finished blanks can contain a machine readable mark to indicate the cylindrical axis of the finished surface. The cylindrical axis of the machined surface should be precisely controlled in reference to the axis of the pre-finished surface.

In another embodiment, the ophthalmic lens in FIG. 5 can be further configured to induce spherical aberration at the central vision for the correction of spherical aberration in an eye. This can be achieved by shaping one of the two toric surfaces with an aspheric component around optical axis.

The ophthalmic lens of in FIG. 5 can further be configured to have aspheric shapes away from the optical axis for reduced off-axis Seidel aberrations. It can also be configured for a bi-focal lens or a progressive lens.

Controlling Cylindrical Power by Arranging Cylinder Axes of Toric Surfaces

Cylindrical powers in a fine resolution can be achieved by arranging the cylinder axes of two toric surfaces with coarse powers. In accordance with the present invention, the method requires two toric surfaces, where one of the two surfaces has a dominant cylindrical power in one direction $\Phi_{A1}$ while the other surface has a small biasing cylindrical power at a different orientation $\Phi_{A2}$. The angle between the two cylinder axes is measured by $\alpha$.

The combined cylindrical power can be expressed by an analytical expression:

$$\Phi_A = \text{SQRT}(\Phi_{A1}*\Phi_{A1}+\Phi_{A2}*\Phi_{A2}+2*\Phi_{A1}\Phi_{A2}*\cos(2\alpha)) \quad (1)$$

where SQRT is the mathematic operator of square root. The combined cylindrical power ΦA is between $(\Phi_{A1}-\Phi_{A2})$ and $(\Phi_{A1}+\Phi_{A2})$, depending on the angle between the two cylinder axes. In one example, if the dominant cylindrical power $\Phi_{A1}$ has a cylindrical power of 1.0 D and the bias cylindrical power is 0.125 D, any cylindrical power in a fine resolution between 0.875 D and 1.125 D can obtained using these two base cylindrical powers. In another example, a base bias cylindrical power of 0.25 D and 12 base dominant cylindrical powers of 0.25 D, 0.75 D, 1.25 D, 1.75 D, 2.25 D, 2.75 D, 3.25 D, 3.75 D, 4.25 D, 4.75 D, 5.25 D, 5.75 D, is used to achieve any cylindrical power between 0.00 D and 6.00 D with a resolution finer than 0.25 D.

There are at least three advantages associated with making a lens with a cylindrical power using two cylinder elements arranged at different cylinder axes. First, a high-resolution, adjustable cylindrical power can be achieved by arranging the relative orientation of the two cylinder axes. Controlling two cylinder axes within 2.5 degree is relatively easy in a manufacture process in comparison to a precise control of surface shape within 0.02 D. Second, making cylinder lenses in a fine resolution of cylindrical power is dramatically simplified and is low-cost because only a limited number of base molds are required. Third, a high-speed process can be achieved by fabricating all lenses with one bias power or just a few biasing cylindrical powers. High-definition lenses can then be custom manufactured just like a conventional lens with a limited number of cylindrical powers. One only needs to pay attention to the relative angle between the two cylinder axes.

It must be mentioned that arranging two cylindrical powers at various orientations will cause a variable focus offset to the base spherical power. The induced spherical power can be expressed as $$\Phi_S = 0.5 * (\Phi_{A1} + \Phi_{A2} - \Phi_A) \quad (2)$$

where $\Phi_{A1}$, $\Phi_{A2}$ and ΦA are the dominate cylindrical power, the biasing cylindrical power and the combined cylindrical power, respectively. The total focus change depends on the angles between the two cylindrical axes, and can be as large as the biasing cylindrical power if the full range of angle between the two cylinder axes is 90 degrees. Because of the focus offset, this cylinder control method cannot be used for making conventional lenses with a resolution of 0.25 D.

When the bias cylindrical power is less than 0.25 D, the focus change in spectacle lenses can be addressed in two different ways. First, for eyes with significant accommodation range, the focus change in Eq (2) can be factored into the total spherical power. Second, for eyes with no or little accommodation, more than one bias power is needed to reduce the induced focus offset in Eq. (2). In this case, one may need five to ten bias powers and use a small angular range for fine tuning the combined cylindrical power.

In addition to making lenses with precise control of cylindrical power, the method of arranging two cylindrical powers described has three other applications. First, precise control of cylindrical power can be achieved even if the bias cylindrical power and the dominant cylinder are known to have manufacturing errors. A compensation angle can be calculated for eliminating the errors in the bias and dominant cylindrical powers. Second, one can use the principle described to build an improved phoroptor for preview of astigmatism-free custom vision corrections. Third, this method can also be used for making customized intra-ocular lenses.

Closed-Loop Methods for Making Customized High-Precision Toric Lenses

Customized spectacles for astigmatism-free refractive correction cannot be manufactured in today's labs using existing technologies because today's spectacle lenses are manufactured in a coarse resolution of 0.25 D and a rough tolerance between +0.09 D to +0.37 D as illustrated in British standard for tolerances on optical properties of mounted spectacle lenses (BS 2738-1:1998). Novel methods are required for making high-precision lenses for an astigmatism-free customized refractive correction.

A method for fabricating a customized toric lens for the high-definition refractive correction of a human eye in accordance with the present invention would utilize a closed-loop process. First, a manufacturer would receive custom correction data for the manufacture of a toric lens with a spherical power, and a cylindrical power in a finer resolution than 0.25 D, e.g., 0.025 D. Second, desired surface profiles for a lens would be determined based on the obtained refractive correction data and the material used for making the ophthalmic lens. Third, a customized toric lens would be fabricated either through lens molding or by surfacing a semi-finished blank based on the determined surface profiles. Fourth, each fabricated custom lens would be measured with a lensometer. The lens would be delivered to a customer only if the measured cylindrical power of the manufactured lens and the cylindrical power of the manufactured lens were within a custom tolerance level between 0.01 D and 0.08 D, e.g., 0.025 D. The lens would be reworked by surfacing at least one of the two surfaces if the difference between the measured cylindrical power of the manufactured lens and the cylindrical power measured by the measuring station is not within a custom tolerance level.

In another embodiment of the present invention, the closed loop process for making a high-precision spectacle lens comprises the steps of: a) obtaining correction data (in some embodiments, a prescription) that comprises a spherical focus power, a cylindrical power, and an optional cylindrical axis and spherical aberration; b) determining desired surface profiles for a lens based on the obtained refractive prescription and the material used for making the ophthalmic lens; c) mounting a component in the form of an optical piece or a partially processed optical element into a manufacture system and altering at least one surface profile of the component according to the determined surface profiles; d) measuring refractive properties of the altered component using a lensometer; f) calculating residual errors of the manufactured lens from the obtained correction data and the measured refractive data of the altered component; e) further changing at least one surface profile of the component based on the calculated residual errors until the residual errors of the manufactured lens are within a custom tolerance between 0.01 D and 0.08 D, e.g., 0.025 D.

Methods for Previewing an Astigmatism-Free Refractive Correction

Even though objective wavefront refractors provide precise measurements of cylindrical power and cylindrical axis of an eye, it is still preferred to preview the cylinder correction before a lens is made for the cylindrical correction.

A phoroptor is a device normally used in an optometry office for the subjective determination of a spherical focus power, a cylindrical power, and a cylindrical axis of an eye. Differences in cylindrical powers for a refractive correction are limited by a resolution of 0.25 D while differences in cylindrical axis are set by a resolution of about 5 degrees. Cylindrical axes in a phoroptor are never precisely related to an objective refraction in optometry practice. Therefore, conventional phoroptors in the prior art are not suited for high-definition refractive correction.

Figure 6:
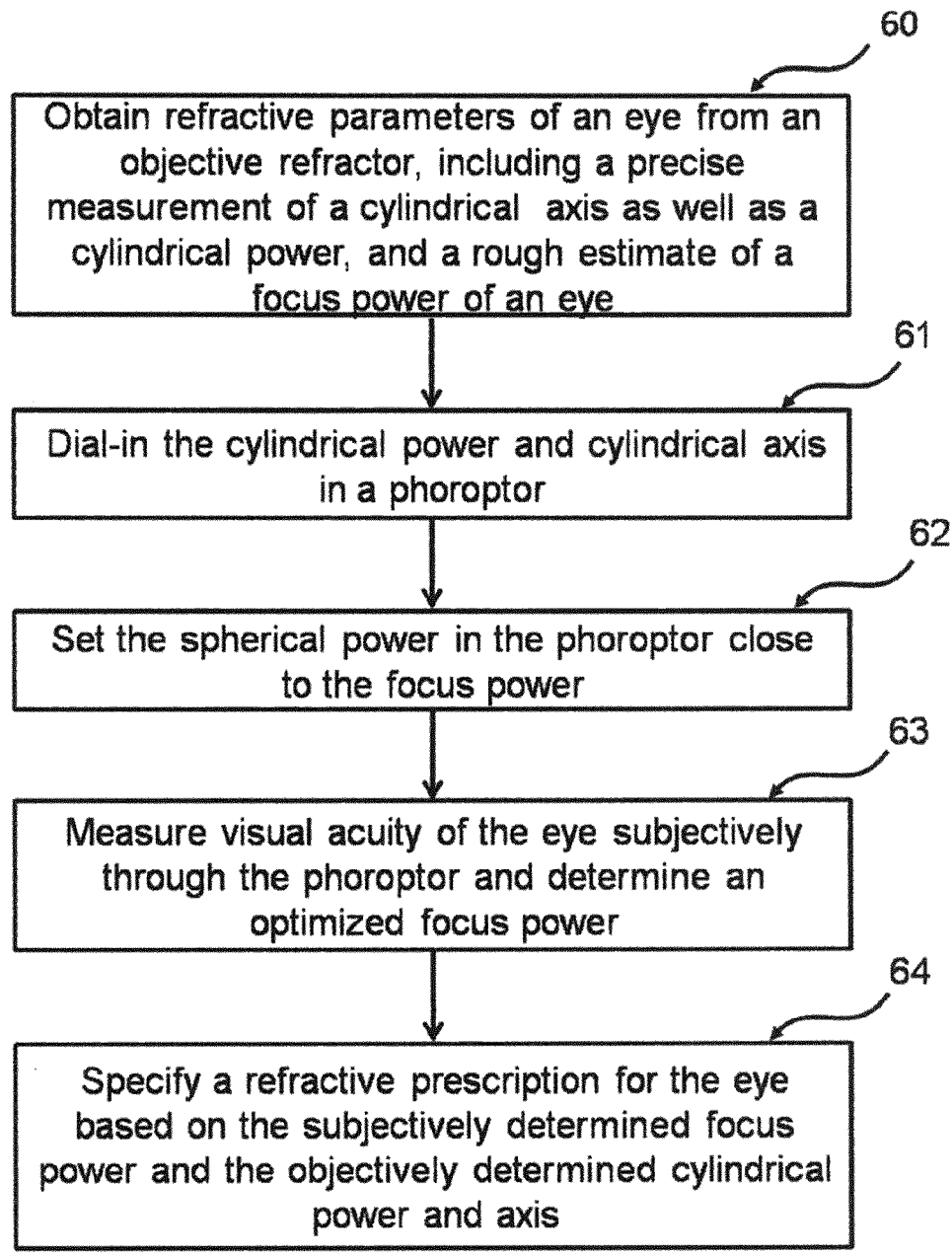
FIG. 6 shows a method for previewing a refractive correction of an eye in accordance with the present invention.

FIG. 6 shows a method for previewing an astigmatism-free refractive correction of an eye in accordance with the present invention. In one embodiment, the method for previewing an astigmatism-free refractive correction of an eye in accordance with the present invention comprises the steps of: a) obtaining correction data of a refractive correction of an eye from an objective refractor 60, wherein the objective refractor measures wavefront slopes across the pupil of an eye, and precisely determines a cylindrical power (at a resolution finer than 0.25 D), a cylindrical axis, an optional spherical aberration, and a rough estimate of a spherical focus power of an eye; b) dialing-in the determined cylindrical power and cylindrical axis in a phoroptor 61, wherein the cylinder parameters are controlled precisely with a resolution finer than 0.25 D; c) setting the spherical focus power to a plurality of values and measure visual acuity of an eye subjectively through phoroptor 62; d) determining an optimized focus power subjectively that sets the eye's accommodation at the far point 63; e) determining the best corrected acuity under preview and provide a refractive prescription 64 based on the subjectively determined focus power and the objectively determined cylindrical power and cylindrical axis.

Improved Phoroptors for Measuring Refractive Errors of an Eye

The method of previewing an astigmatism-free refractive correction in accordance with the method described above may be achieved using a phoroptor equipped with a wavefront aberrometer. In one embodiment, such an advanced phoroptor would comprise the following modules: a wavefront sensing module for providing an instant and objective measurement of an eye's aberrations; an output module for displaying the measured aberrations that include at least a focus error, a cylindrical axis and a cylindrical power in a resolution finer than 0.25 D, e.g., 0.025 D; a mechanical mechanism for moving the wavefront aberrometer to a position for measuring the eye's aberrations as well as for moving the wavefront aberrometer away from the optical axis of the eye for other measurements of the eye, a phoroptor module for performing subjective refraction of an eye using a plurality of spherical lenses and cylindrical lenses, wherein the phoroptor module may not correct high-order aberrations such as spherical aberration and coma; and a mechanism in the phoroptor module for dialing in a cylindrical power and cylindrical axis obtained from the output device of the wavefront aberrometer so that an astigmatism-free vision correction is achieved. The wavefront module would also measures all aberrations in the eye and provide image metrics derived from the measured aberration in the eye.

By design, conventional phoroptors in the prior art are not suited for astigmatism-free refractive corrections. An improved phoroptor must address the issues of relating the cylindrical axis of the phoroptor to the orientation of the eye in an objective refractor, and controlling cylindrical power in a resolution much finer than 0.25 D.

Figure 7:
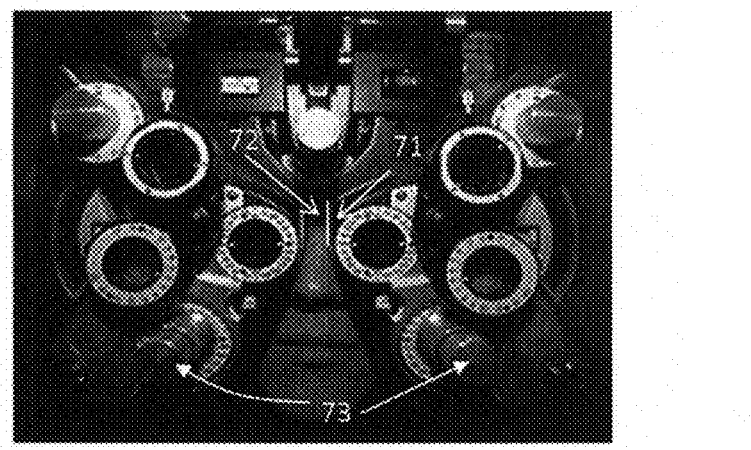
FIG. 7 shows a phoroptor for subjective refraction of an eye in accordance with the present invention.
Figure 7:
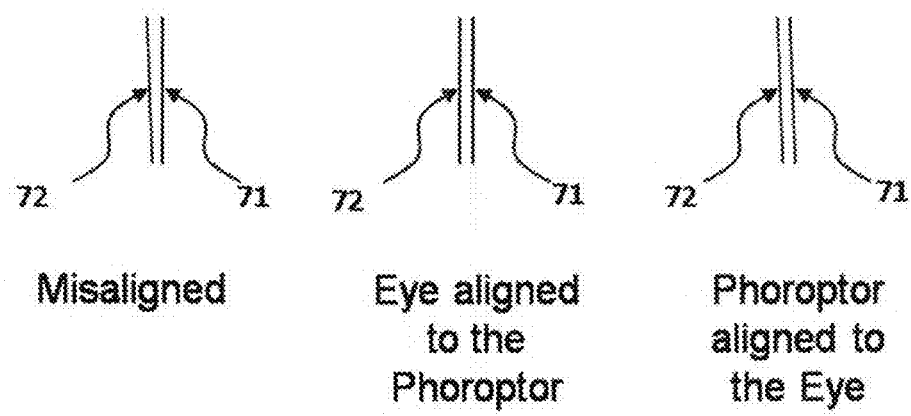

FIG. 7 shows an improved phoroptor for inclusion in the measuring station to allow for subjective refraction of an eye in accordance. A registration mark 72 is placed on face of a patient. An objective refraction of the eye can be obtained with its cylindrical axis relating to the alignment mark 72. When the same eye is placed behind a phoroptor, a light beam 71 from the phoroptor can be placed next to the registration mark for relating the cylindrical axis of the phoroptor to an orientation of the eye in another measurement.

Relating the cylindrical axis of a phoroptor to an orientation of an eye in an objective refractor may involve using the aid of a mechanical device, a light beam, a projected image, or an image device. Relating the cylindrical axis of a phoroptor to the cylindrical axis of an eye in an objective refractor may also involve comparing a fixed orientation such as an alignment mark 71 attached to a phoroptor to an orientation of an eye such as a registration mark 72 on the face of a patient or in an eye. Relating the cylindrical axis of a phoroptor to the cylindrical axis of an eye in an objective refractor may involve adjusting an orientation such as an alignment mark 71 attached to a phoroptor to match to an orientation of an eye specified by a registration mark 72 on the face of a patient or in an eye, and determining an angular offset from the adjustment to the alignment mark attached to the phoroptor.

The improved phoroptor associated with the measuring station further includes a digital control and display of its cylindrical axis instead of a manual control of the cylindrical axis 73. The digital control may be achieved using motorized control of the cylindrical axis.

The improved phoroptor can further include a mechanism for achieving cylinder correction continuously instead of every 0.25 D as in conventional phoroptors.

The improved phoroptor can further include a mechanism for achieving refractive correction of spherical aberrations in an eye using a plurality of phase plates or a plurality of lenses with aspheric surface profiles.

Figure 8:
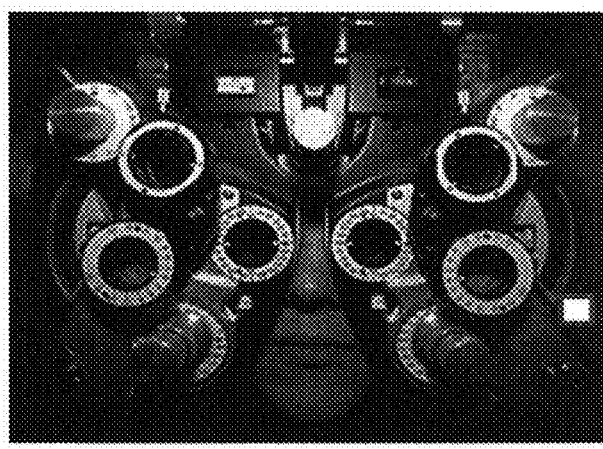
FIG. 8 shows another phoroptor for subjective refraction of an eye in accordance with the present invention.

In another embodiment, an improved phoroptor for subjective refraction of an eye includes a mechanism for entering a cylindrical power and a cylindrical axis manually or for importing refractive data from an objective refractor for improved efficiency and accuracy. Such a phoroptor is illustrated in FIG. 8 and comprises: a) a plurality of spherical lenses for the correction of defocus in an eye; b) a plurality of cylindrical lenses for the correction of astigmatism in an eye; c) a mechanism 81 for importing refractive data from an objective refractor.

Improved Objective Refractors for Refractive Correction of an Eye

A conventional wavefront aberrometer determines cylindrical error with high accuracy, but is not sufficient for astigmatism-free refractive correction. This is because conventional wavefront aberrometers do not provide a reliable measurement of spherical focus power for setting an eye to its far accommodation point, and do not contain a mechanism to precisely link the cylindrical axis measured in an objective refractor to the cylindrical axis in a phoroptor for a subjective refraction or an ophthalmic lens.

Figure 9:
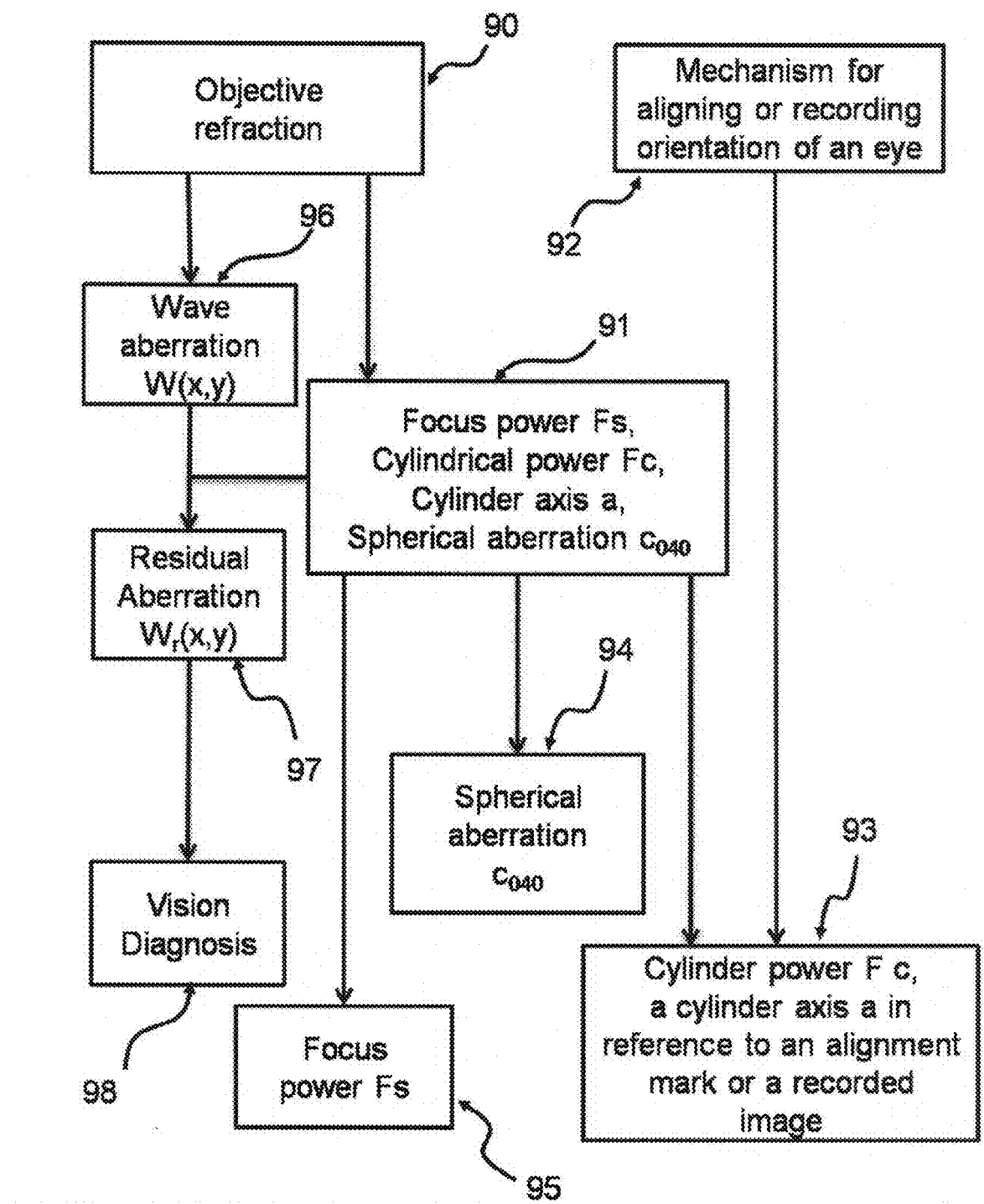
FIG. 9 shows a flow chart for an improved method for a manifest refraction in accordance with the present invention.

FIG. 9 shows an improved objective refractor system for a refractive correction. The system comprises an objective refraction device 90 for measuring refractive errors of an eye including at least a cylindrical power, a cylindrical axis, and a spherical focus error without any subjective response, and a mechanism for aligning orientation of an eye to a predetermined direction in the objective refractive device or for recording the facial orientation of an eye during an objective refraction 92.

In one embodiment, the objective refraction device 90 is an objective aberrometer that measures wavefront slopes across the pupil of an eye. The wavefront aberrometer provides at least a spherical focus power, a cylindrical power, a cylindrical axis, and an optional spherical aberration of an eye to storage element 91. The focus power and optional spherical aberration are available on output devices 95 and 94 respectively.

The mechanism for aligning or recording orientation of an eye 92 in one embodiment allows changing relative orientation of an eye to a predetermined direction in the objective refraction device, and provides a visual aid for setting up the relative orientation between the refraction device and the eye under test. In combination with the data in storage element 91, the objective refractor system is able to output a cylindrical power and cylindrical axis in reference to the alignment mark or recorded image in output device 93.

The mechanism for aligning or recording facial orientation of an eye 92 in one embodiment uses a digital camera to record at least a portion of a human face. The human face may include a computer-generated (via the measuring station) alignment mark, in the form of a frame for a spectacle lens without a refractive element.

In another embodiment, the objective refraction device can further provide total wave aberration of an eye 96, and vision diagnosis 98 based on the total wave aberration, data from a refractive correction, and a residual wave aberration 97, wherein the refractive correction includes a spherical focus power, a cylindrical power, a cylindrical axis, and an optional spherical aberration.

An Improved Manifest Refraction for Refractive Corrections

With the improved phoroptor and wavefront aberrometer provided as part of the measuring station according to the present invention, an improved method of manifest refraction for astigmatism-free customized refractive correction is provided. The method comprises of the following steps. First, an artificial registration mark is placed on a human face. Second, an objective estimation of the eye's focus error, cylindrical power, and cylindrical axis is obtained using an objective refractor. The focus power from the objective refraction has a resolution of 0.25 D and the cylindrical power has a resolution finer than 0.25 D, e.g. 0.025 D. The objective refractor is preferably a wavefront aberrometer. Third, orientation information of an eye in reference to the objective refractor is stored based on the artificial mark placed on the face. Fourth, before performing subjective refraction with a phoroptor, the tested eye in a phoroptor is aligned or checked based on the stored orientation information of an eye. Fifth, the measuring station dials in a cylindrical correction matching the obtained cylindrical power and cylindrical axis from the objective refractor. Sixth, a plurality of spherical corrections in addition to the dialed-in cylindrical correction is presented to the patient by the station. A revised focus power is obtained as an improvement over the objectively measured focus error to offer an optimized correction of an eye for far vision. Seventh, refractive correction data for manufacture of an ophthalmic lens is generated by combining the objectively determined cylindrical refractive power and axis and the subjectively revised focus power.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those skilled in the art, without departing from the spirit and scope of the present invention, which is more particularly set forth in the appended claims. Furthermore, those skilled in the art will appreciate that the foregoing description is by way of example only, and is not intended to limit the invention.

What is claimed is:

1. A method for providing a pair of sunglasses to an individual, including individuals with a visual acuity of 20/20 or better, comprising the steps of:
    providing a measuring station configured for automatic data acquisition without necessary intervention from a human other than the individual, the measuring station configured to:
        obtain an objective measurement of wave aberration from each eye of the individual;
        determine a measured cylindrical power and cylindrical axis from the objective measurement of wave aberration;
        place a plurality of lenses according to the measured cylindrical power and cylindrical axis from the objective measurement of wave aberrations from each eye of the individual into a correction device for the individual to see through and read at least one acuity chart;
        allow the individual to manually adjust the focus power of the correction device;
        accept results from the individual in reading the acuity chart through the correction module for each eye; and
        determine a focus power of each eye through subjective refraction, wherein the subjective refraction involves subjective responses from the individual to a plurality of focus powers;
    generating correction data for making the pair of sunglasses;
    transmitting data for making the pair of sunglasses via an electronic media, wherein the transmitted data contains at least the correction data for making the pair of sunglasses;
    manufacturing lenses for the sunglasses based on the correction data;
    fitting the lenses into frames to produce finished sunglasses; and
    providing the finished pair of sunglasses to the individual.

2. The method of claim 1, wherein the pair of sunglasses is an over-the-counter sunglass that does not require a prescription.

3. The method of claim 1, wherein transmitting data for making the pair of sunglasses further includes at least one of following for reviewing and checking by a human other than the individual: a) records for the obtained objective measurement of wave aberration from each eye of the individual, b) results of the individual in reading the acuity chart through the correction device for a plurality of focus powers, and c) a near focus power of the individual for reading near tasks.

4. The method of claim 3, wherein the measuring station is further configured to allow the human other than the individual to review the transmitted data and send feedback data to the measuring station.

5. The method of claim 1, wherein the measuring station further is configured to offer to and receive from the individual a selection of sunglass frames.

6. The method of claim 5, wherein the generated correction data for making the pair of sunglasses is modified to take into account the shape of the selected sunglass frames.

7. The method of claim 5, wherein the measuring station further is configured to take a picture of the individual with and/or without the selected pair of sunglasses.

8. The method of claim 1, wherein the measuring station further is configured to accept payment information from the individual.

9. The method of claim 1, wherein the measuring station further is configured to accept delivery information from the individual.

10. The method of claim 1, wherein the measuring station further is in communication with a lens fabricator and is configured to transfer the correction data to the lens fabricator to manufacture custom lenses.

11. The method of claim 10, wherein the lens fabricator is automated.

12. The method of claim 11, wherein the measuring station is in communication with the automated lens fabricator and is configured to transfer the correction data and delivery information from the individual to a lens fabricator to manufacture custom lenses.

13. The method of claim 11, wherein the measuring station further is configured to offer to and receive from the individual selected sunglass frame styles.

14. The method of claim 13, wherein the automated lens fabricator is further configured to assemble the manufactured custom lenses with the selected sunglass frames.

15. The method of claim 10, wherein the measuring station further is configured to accept payment information and delivery information from the individual.

16. The method of claim 10, wherein based on the correction data for each eye, off-the-shelf lenses are selected for the individual.

17. The method of claim 1, wherein the lenses are manufactured by molding or by machining.

18. The method of claim 1, wherein the measuring station comprises a wavefront phoroptor for measuring refractive corrections of a focus error and a cylinder error for an eye, wherein the wavefront phoroptor comprises:
 a wavefront sensing module for providing the objective measurement of aberrations of the eye, measuring wavefront slopes across a pupil, and determining wave aberration of the eye that includes at least a cylindrical axis and a cylindrical power in a resolution finer than 0.25 D; and
 a phoroptor module with a plurality of spherical lenses and cylindrical lenses and an acuity chart for subjectively determining the focus error of the eye.

19. The method of claim 18, wherein the cylindrical lenses are set according to the objective measurement of aberrations from the wavefront sensing module; and wherein the subjectively determined focus error involves subjective responses by the individual to a plurality of focus powers by the eye viewing an acuity chart.

20. The method of claim 18, wherein the wavefront sensing module measures aberrations of the eye using a lenslet array wavefront sensor.

21. The method of claim 18, wherein the objective measurement further includes a focus error, a spherical aberration, a coma and other high-order aberrations, and wherein the cylinder power and the cylinder angle is determined for optimized vision from the determined wave aberration across a pupil of the eye.

22. A measuring station configured for automatic data acquisition without necessary intervention from a human other than the individual, the measuring station configured to:
 a. obtain an objective measurement of wave aberration from each eye of the individual;
 b. determine a measured cylindrical power and a cylindrical axis from the objective measurement of wave aberration;
 c. place a plurality of lenses according to the determined measured cylindrical power and a cylindrical axis into a correction module for the individual to see through and read an acuity chart;
 d. allow the individual to manually adjust the focus power of the correction device;
 e. accept results from the individual in reading the acuity chart through the correction module for each eye;
 f. determine a focus power of each eye through subjective refraction, wherein the subjective refraction involves subjective responses from the individual from a plurality of focus power corrections; and
 g. communicate the measured cylindrical power, cylindrical axis and focus power of each eye to a lens fabricator to manufacture custom lenses or to a repository of off-the-shelf lenses.

23. The measuring station of claim 22, wherein the measuring station further is configured to transmit data for review by a human other than the individual, wherein the transmitted data includes at least one of a) records for the obtained objective measurement of wave aberration from each eye of the individual, and b) results of the individual in reading the acuity chart through the correction device for a plurality of focus powers.

24. The measuring station of claim 22, wherein the measuring station further is configured to take a picture of the individual.

25. The measuring station of claim 22, further comprising a wavefront phoroptor for measuring refractive corrections of a focus error and a cylinder error for an eye, comprising:
 a wavefront sensing module for providing the objective measurement of aberrations of the eye, wherein the wavefront sensing module measures wavefront slopes across a pupil and determines wave aberration of the eye that includes at least a cylindrical axis, and a cylindrical power in a resolution finer than 0.25 D; and
 a phoroptor module with a plurality of spherical lenses and cylindrical lenses and an acuity chart for subjectively determining a focus error of an eye.

26. The measuring station of claim 22, further configured to offer to and receive from the individual a selection of sunglass frames.

27. The measuring station of claim 22, further configured to accept payment information from the individual.

28. The measuring station of claim 22, further configured to accept delivery information from the individual.

29. A system for providing a pair of sunglasses to an individual, including individuals with a visual acuity of 20/20 or better, comprising:
 a. a measuring station configured for automatic data acquisition without necessary intervention from a human other than the individual to obtain an objective measurement of wave aberration from each eye of the individual and determine a measured cylindrical power and a cylindrical axis from the objective measurement of wave aberration; place a plurality of lenses according to the determined cylindrical power and cylindrical axis into a correction module for the individual to see through and read an acuity chart; and determine a focus power of each eye through subjective refraction, wherein the subjective refraction involves subjective responses from the individual from a plurality of focus powers; and
 b. a lens fabricator to manufacture custom lenses or a lens repository to provide off-the-shelf lenses according to the measured cylindrical power, cylindrical axis and focus power.

30. The system of claim 29, wherein the measuring station further comprises a wavefront sensing module for providing the objective measurement of aberrations of the eye, wherein the wavefront sensing module measures wavefront slopes across a pupil and determines wave aberration of the eye that includes at least a cylindrical axis, and a cylindrical power in a resolution finer than 0.25 D; and a phoroptor module with a plurality of spherical lenses and cylindrical lenses and an acuity chart for subjectively determining a focus error of an eye.

31. The system of claim 29, further comprising a database configured to receive payment and delivery information from the individual.

32. A method for providing a pair of prescription eyeglasses to an individual, including individuals with a visual acuity of 20/20 or better, comprising the steps of:
providing a measuring station to the individual, the measuring station configured to automatically:
obtain an objective measurement of wave aberration from each eye of the individual;
determine a measured cylindrical power and a cylindrical axis from the objective measurement of wave aberration;
place a plurality of lenses according to the determined cylindrical power and a cylindrical axis from the objective measurement of wave aberration into a correction device for the individual to see through and read an acuity chart;
allow the individual to manually adjust the focus power of the correction device;
accept results from the individual in reading the acuity chart through the correction module for each eye; and
determine a focus power of each eye through subjective refraction, wherein the subjective refraction involves subjective responses from the individual to a plurality of refractive corrections;
generating correction data from which to manufacture lenses;
manufacturing the lenses or selecting a set of off-the-shelf lenses appropriate for the correction data;
fitting the lenses into frames to produce finished eyeglasses; and
providing the finished eyeglasses to the individual.

33. A kiosk system for prescriptive eyeglasses, configured for automatic data acquisition without necessary intervention from a human other than the individual, comprising:
a. a wavefront sensing module for providing objective measurement of aberrations of the eye, wherein the wavefront sensing module measures wavefront slopes across a pupil and determines wave aberration of the eye that includes at least a cylindrical axis, and a cylindrical power in a resolution finer than 0.25 D;
b. a vision correction module for presenting a plurality of refractive corrections for the individual to see through, wherein the plurality of refractive corrections includes: a cylindrical power and a cylindrical axis according to the determined wave aberrations, and a plurality of focus power corrections that is controlled manually by the individual;
c. an acuity chart for determining visual acuity of the eye under the plurality of focus power corrections,
d. a human-to-machine interface module to accept results from the individual in reading the acuity chart through the correction module for a plurality of focus power corrections;
e. an exporting module for communicating data to a lens fabricator to manufacture custom lenses or to a repository of off-the-shelf lenses, wherein the communicated data includes at least one of the following: the measured cylindrical power, cylindrical axis and focus power of each eye; records of the wavefront module for data review; and results of the individual in reading the acuity chart through the correction device for a plurality of focus power corrections.

34. The kiosk system of claim 33, further comprising a device configured to offer to and receive from the individual a selection of frames.

35. The kiosk system of claim 34, further comprising a device configured to take a picture of the individual with and/or without the selected sunglass frames.

36. The kiosk system of claim 33, further comprising a device configured to offer to accept payment information from the individual.

37. The kiosk system of claim 33, further comprising a device configured to offer to accept delivery information from the individual.

* * * * *